United States Patent
Winek et al.

(10) Patent No.: US 11,744,939 B2
(45) Date of Patent: Sep. 5, 2023

(54) CYCLIC INTRATHECAL DRUG DELIVERY SYSTEM AND BIOMARKER MONITORING

(71) Applicant: Medtronic, Inc., Minneapolis, MN (US)

(72) Inventors: Michael E. Winek, Minneapolis, MN (US); Lauren E. Barth, Minneapolis, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 482 days.

(21) Appl. No.: 16/949,418

(22) Filed: Oct. 29, 2020

(65) Prior Publication Data

US 2022/0133989 A1    May 5, 2022

(51) Int. Cl.
*A61M 5/142*    (2006.01)
*A61M 5/172*    (2006.01)
(Continued)

(52) U.S. Cl.
CPC .... *A61M 5/14276* (2013.01); *A61M 5/14212* (2013.01); *A61M 5/1582* (2013.01); *A61M 5/16809* (2013.01); *A61M 5/172* (2013.01); *A61M 25/0026* (2013.01); *A61M 27/006* (2013.01); *A61M 2005/14208* (2013.01); *A61M 2205/3553* (2013.01); *A61M 2205/52* (2013.01)

(58) Field of Classification Search
CPC .......................... A61M 5/14212–1424; A61M 5/14276–2005/14284; A61M 27/006
See application file for complete search history.

(56) References Cited

U.S. PATENT DOCUMENTS

| 4,360,019 A | 11/1982 | Portner et al. |
| 4,472,263 A | 9/1984 | Garg et al. |

(Continued)

FOREIGN PATENT DOCUMENTS

| DE | 102008003330 A1 | 7/2009 | |
| WO | WO 2013/052414 A2 | 4/2013 | |
| WO | WO-2020149993 A1 * | 7/2020 | ........... A61K 31/197 |

OTHER PUBLICATIONS

Extended European Search Report for European Application No. 19202531.0, dated Jan. 27, 2020, 12 pgs.

(Continued)

*Primary Examiner* — Jenna Zhang
(74) *Attorney, Agent, or Firm* — Patterson Thuente, P.A.

(57) ABSTRACT

Intrathecal drug delivery pumps can aspirate cerebrospinal fluid (CSF) when the drug reservoir is empty or at other times to maintain a continuous or cyclic fluid flow through the pump and the delivery catheter. This addresses the potential need for continuous infusion to maintain an un-occluded fluid pathway to the intrathecal space by providing an "active port" that aspirates and expels CSF to keep fluid flow going without infusing a drug or requiring saline to fill the pump. If drug refill visits are missed, CSF could be used to keep the pump mechanism functional rather than having it run dry requiring replacement or requiring saline injections to keep the pump mechanism functioning. In addition, by having the pump aspirate CSF into the body of the pump, it would be possible to monitor biomarkers using systems in the fluid pathway and pressure differences for possible issues related to CSF management.

17 Claims, 6 Drawing Sheets

(51) Int. Cl.
*A61M 5/168* (2006.01)
*A61M 5/158* (2006.01)
*A61M 25/00* (2006.01)
*A61M 27/00* (2006.01)

(56) References Cited

U.S. PATENT DOCUMENTS

| | | | |
|---|---|---|---|
| 4,573,994 | A | 3/1986 | Fischell et al. |
| 5,217,442 | A | 6/1993 | Davis |
| 5,637,083 | A | 6/1997 | Bertrand et al. |
| 6,283,943 | B1 | 9/2001 | Dy et al. |
| 6,579,280 | B1 | 6/2003 | Kovach et al. |
| 6,805,687 | B2 | 10/2004 | Dextradeur et al. |
| 6,962,580 | B2 | 11/2005 | Adams et al. |
| 7,044,932 | B2 | 5/2006 | Borchard et al. |
| 7,072,802 | B2 | 7/2006 | Hartlaub |
| 7,255,682 | B1 | 8/2007 | Bartol, Jr. et al. |
| 7,637,897 | B2 | 12/2009 | Ginggen |
| 7,799,016 | B2 | 9/2010 | Shachar et al. |
| 7,942,863 | B2 | 5/2011 | Kalpin et al. |
| 8,535,280 | B2 | 9/2013 | Rogers et al. |
| 8,721,605 | B2 | 5/2014 | Brandt et al. |
| 9,122,785 | B2 | 9/2015 | Alme et al. |
| 9,421,325 | B2 | 8/2016 | Kalpin |
| 9,590,352 | B2 | 3/2017 | Bilbrey et al. |
| 10,434,251 | B2 | 10/2019 | Anand et al. |
| 10,441,770 | B2 | 10/2019 | Singh et al. |
| 2002/0022793 | A1 | 2/2002 | Bertrand et al. |
| 2003/0181888 | A1 | 9/2003 | Dextradeur et al. |
| 2005/0187515 | A1 | 8/2005 | Varrichio et al. |
| 2006/0089619 | A1 | 4/2006 | Ginggen |
| 2006/0089620 | A1 | 4/2006 | Gibson et al. |
| 2006/0229548 | A1 | 10/2006 | Cull |
| 2006/0247737 | A1 | 11/2006 | Olson et al. |
| 2007/0255227 | A1 | 11/2007 | Haase |
| 2008/0243093 | A1 | 10/2008 | Kalpin et al. |
| 2011/0068885 | A1 | 3/2011 | Fullerton et al. |
| 2011/0301575 | A1 | 12/2011 | Miesel et al. |
| 2012/0053514 | A1 | 3/2012 | Robinson et al. |
| 2013/0116665 | A1 | 5/2013 | Humayun et al. |
| 2014/0228765 | A1 | 8/2014 | Burke et al. |
| 2016/0015957 | A1 | 1/2016 | Tieck et al. |
| 2016/0354540 | A1* | 12/2016 | Kalpin ............... A61M 5/1684 |
| 2017/0043151 | A1 | 2/2017 | Bellrichard et al. |
| 2017/0325685 | A1* | 11/2017 | Shachar ............... A61B 5/6868 |
| 2018/0154074 | A1 | 6/2018 | Blomme et al. |
| 2018/0185058 | A1 | 7/2018 | Anand et al. |
| 2019/0060565 | A1 | 2/2019 | Gyory |
| 2020/0001059 | A1 | 1/2020 | Campbell et al. |
| 2020/0121849 | A1* | 4/2020 | Christenson ...... A61M 5/14276 |
| 2020/0121850 | A1* | 4/2020 | Christenson ........ A61M 5/1413 |
| 2021/0268175 | A1 | 9/2021 | Winek |
| 2021/0268176 | A1 | 9/2021 | Winek et al. |

OTHER PUBLICATIONS

International Search Report and Written Opinion corresponding to PCT/US2021/070190 dated Jun. 4, 2021, 12 pgs.

Application and File History for U.S. Appl. No. 16/803,216, filed Feb. 27, 2020, Inventors Winek et al.

Application and File History for U.S. Appl. No. 16/168,358, filed Oct. 23, 2018, now U.S. Pat. No. 11,147,918, dated Oct. 9, 2021, inventors Christenson et al.

Application and File History for U.S. Appl. No. 16/168,399, filed Oct. 23, 2018, inventors Christenson et al.

Application and File History for U.S. Appl. No. 16/803,269, filed Feb. 27, 2020, inventors Winek et al.

* cited by examiner

CYCLIC INTRATHECAL DRUG DELIVERY SYSTEM AND BIOMARKER MONITORING

FIELD

The present disclosure is generally related to implantable medical devices and more particularly to pumps for delivering and/or circulating fluid in the intrathecal space.

BACKGROUND

A variety of medical devices are used for chronic or long-term delivery of therapy to patients suffering from a variety of conditions, such as chronic pain, tremor, Parkinson's disease, cancer, epilepsy, urinary or fecal incontinence, sexual dysfunction, obesity, spasticity, or gastroparesis. For example, pumps or other fluid delivery devices can be used for chronic delivery of therapeutic medicaments, such as drugs or other agents. Typically, such devices provide therapy continuously or periodically according to programmed parameters. The programmed parameters can specify the therapeutic regimen (e.g., the rate, quantity, and timing of medicament delivery to a patient), as well as other functions of the medical device.

Implantable medical infusion pumps are typically implanted at a location within the body of a patient (typically a subcutaneous region in the lower abdomen) and are configured to deliver a fluid medicament through a catheter. The catheter is generally configured as a flexible tube with a lumen running the length of the catheter to a selected delivery site in the body, such as the intracranial or subarachnoid space.

Various types of implantable medical pumps are in use for dispensing medication within the body. These devices either have reservoirs which are to be filled for dispensation on a time-release basis, such as an implantable drug dispenser, or have ports for insertion of medication that is dispensed through an implantable catheter, commonly known as an access port. Often, patients schedule regular drug refill visits to periodically have a medical provider refill the reservoir. If such visits are missed or not scheduled frequently enough, the drug reservoir may be empty for an extended period of time. When there is no fluid flow through the catheter due to an empty reservoir, the catheter can become occluded due to tissue encapsulation which can lead to damage to the pump and the pump can further become damaged if it is operated dry.

SUMMARY

The techniques of this disclosure generally relate to intrathecal drug delivery pumps that can aspirate cerebrospinal fluid (CSF) when the drug reservoir is empty, or at other desired times, to maintain a continuous or cyclic fluid flow through the pump and the delivery catheter or to facilitate other functions of the device. The disclosed pump concept addresses the potential need for continuous infusion to maintain an un-occluded fluid pathway to the intrathecal space by providing an "active port" that aspirates and expels CSF to keep fluid flow going without necessarily infusing a drug or requiring saline or other fluid to fill the pump. If drug refill visits are missed, CSF could be used to keep the pump mechanism functional rather than having it run dry requiring replacement or requiring saline or other fluid injections to keep the pump mechanism functioning. In addition, by having the pump aspirate CSF into the body of the pump, it would be possible to monitor biomarkers using systems in the fluid pathway and/or pressure differences for possible issues related to CSF management.

In one aspect, the present disclosure provides an implantable medical pump configured for bidirectional fluid flow between the pump and a target location in the body. Pump can include a pump housing configured to be subcutaneously implanted into a patient, a medicament reservoir contained within the pump housing configured to contain a medicament and at least one catheter extending from the pump housing to a target location in a body of a patient in fluid communication with the medicament reservoir. A pump mechanism can deliver medicament from the medicament reservoir to the target location. A processor can be configured to control delivery of medicament from the medicament reservoir to the target location with the pump mechanism and can be configured to operate the pump mechanism to aspirate fluid from the target location back into the reservoir and deliver the aspirated fluid back to the target location.

In another aspect, the disclosure provides an implantable medical pump configured for bidirectional fluid flow between the pump and a target location in the body. Pump can include a pump housing configured to be subcutaneously implanted into a patient, a medicament reservoir contained within the pump housing configured to contain a medicament and at least one catheter extending from the pump housing to a target location in a body of a patient in fluid communication with the medicament reservoir. A pump mechanism can be configured to deliver medicament from the medicament reservoir to the target location. A processor can control delivery of medicament from the reservoir to the target location with the pump mechanism and can be configured to operate the pump mechanism to aspirate fluid from the target location back into the pump housing. A sensor can be in communication with the fluid aspirated from the target location back into the pump housing to monitor one or more biomarkers in the fluid.

In some embodiments, an implantable medical pump configured for bidirectional fluid flow can provide generally continuous fluid flow by aspirating fluid from the target location into the medicament reservoir and delivering the fluid from the target location back to the target location when the medicament reservoir does not contain medicament. In other embodiments, such a pump can provide generally continual fluid flow through the at least one catheter by periodically aspirating fluid from the target location into the medicament reservoir and periodically delivering the fluid from the target location back to the target location at regular intervals when the medicament reservoir does not contain medicament.

In some embodiments, an implantable medical pump configured for bidirectional fluid flow can do so through a single catheter having a single lumen to both deliver medicament and fluid from the target location to the target location and aspirate fluid from the target location into the medicament reservoir. In other embodiments, such a pump can include a first catheter to deliver medicament and fluid from the target location to the target location and a second catheter to aspirate fluid from the target location into the medicament reservoir. In further embodiments, such a pump can include a single multi-lumen catheter having a first lumen to deliver medicament and fluid from the target location to the target location and a second lumen to aspirate fluid from the target location into the medicament reservoir.

The details of one or more aspects of the disclosure are set forth in the accompanying drawings and the description below. Other features, objects, and advantages of the tech-

Figure 1:
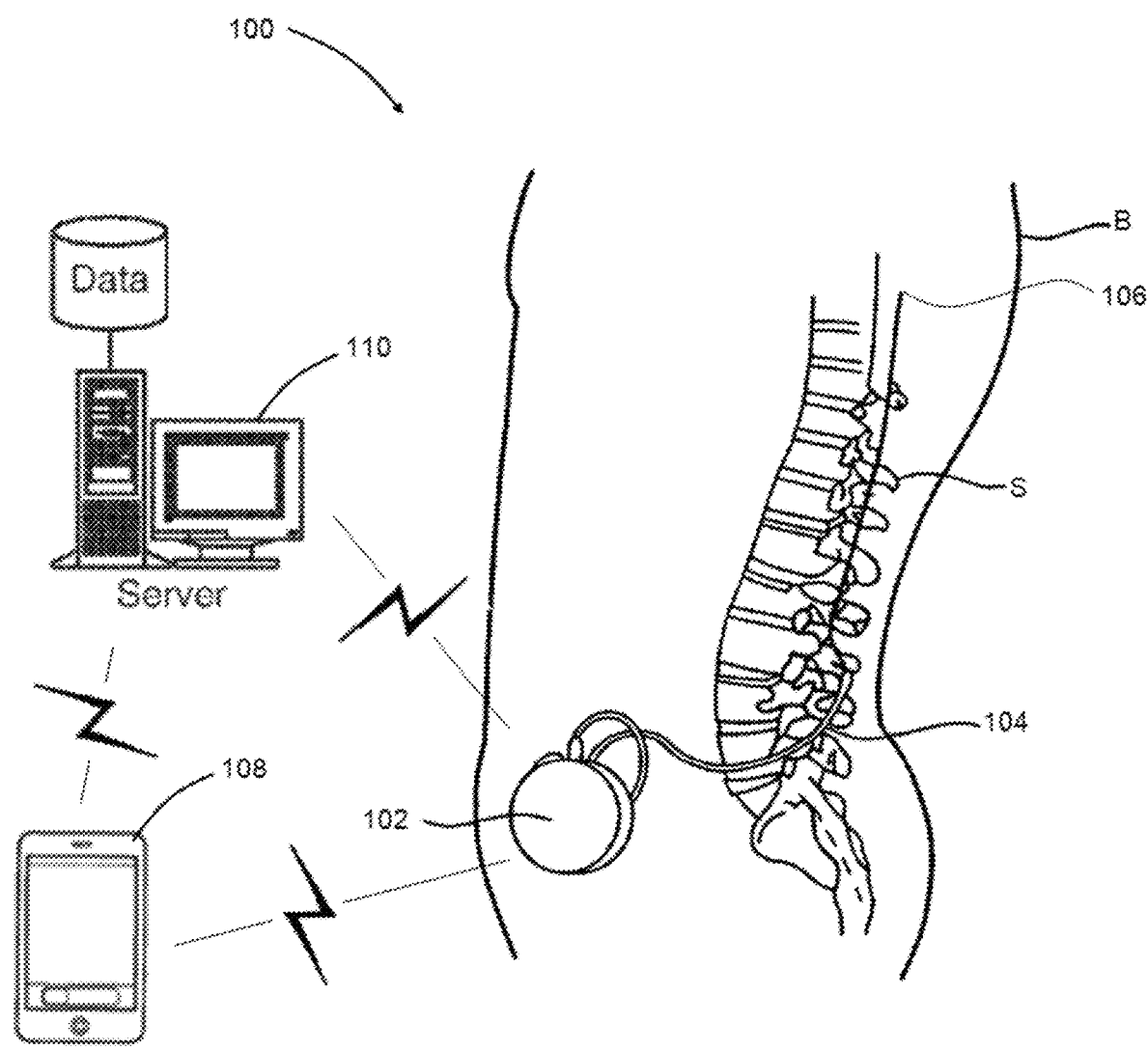
FIG. 1 is a schematic view depicting medicament delivery system in accordance with an embodiment of the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a schematic view of a medicament delivery system 100 is depicted in accordance with an embodiment of the disclosure. The medicament delivery system 100 can include an implantable medical pump 102 and a catheter 104. As depicted, the implantable medical pump 102 can be implanted within the body B of a patient. The implantable medical pump 102 can be in fluid communication with the catheter 104 having a distal tip 106 positioned within, for example, the subarachnoid or intrathecal space of the patient's spinal column S to enable intrathecal delivery of medicament through a lumen of the catheter 104. In other embodiments, the distal tip 106 can be positioned within the intracranial space, or other areas within the patient for targeted delivery of medicament. In one embodiment, the medicament delivery system can further include an optional external programmer 108 and/or an optional server 110 configured to communicate with the implantable medical pump 102 and/or with one another. In some examples, pump 102 may be enabled for bidirectional flow of fluid through catheter 104 to inhibit formation of occlusions and/or for monitoring of biomarkers.

Figure 2:
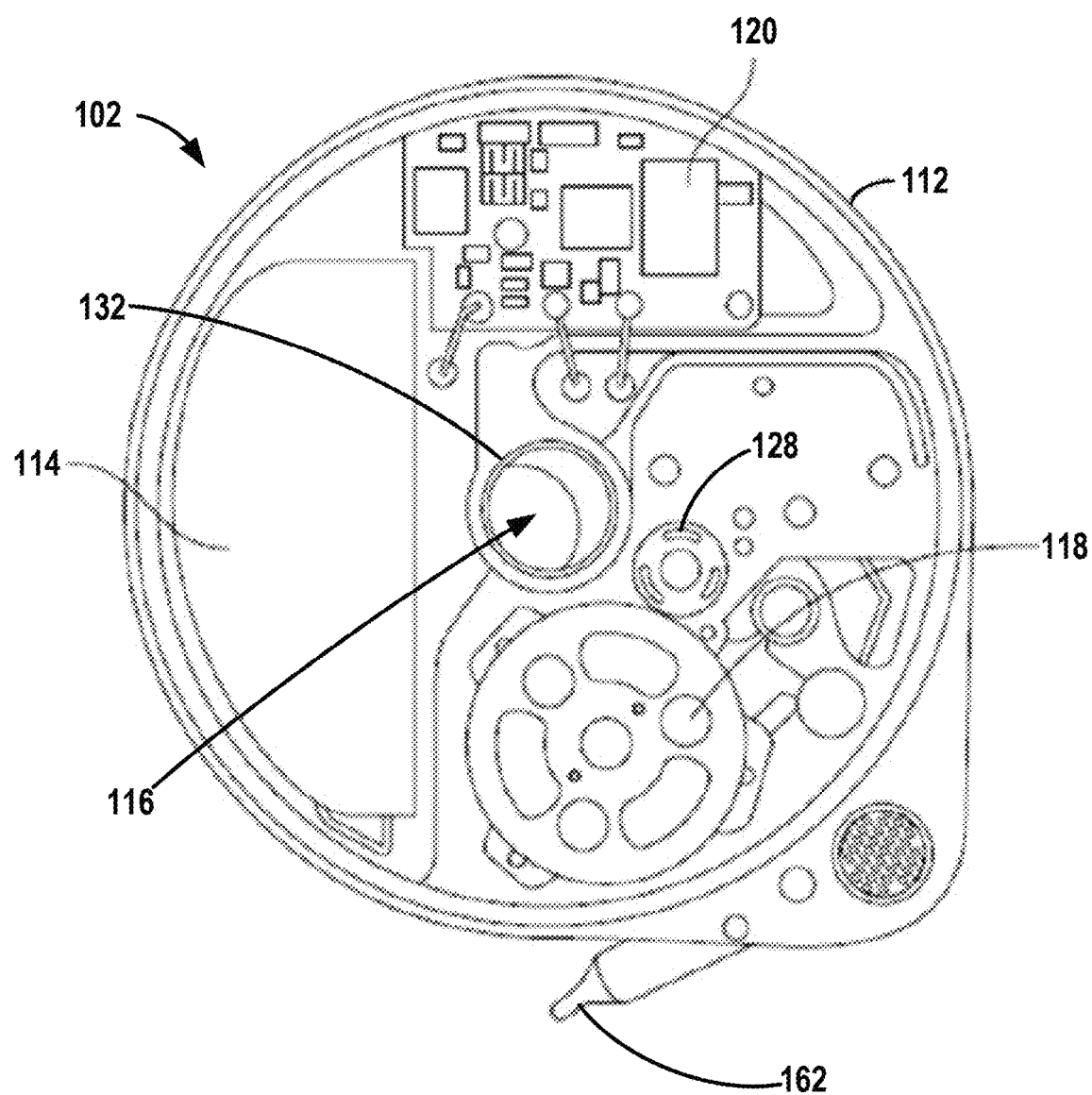
FIG. 2 is a cross-sectional view of an implantable medical pump in accordance with an embodiment of the disclosure

FIG. 2 depicts a cross-sectional plan view of an implantable medical pump 102 in accordance with an embodiment. Implantable medical pump 102 can generally include a housing 112, power source 114, medicament reservoir 116, pump mechanism 118, electronic components 120, a refill port 132 and a catheter port 162 for connection to a catheter. The housing 112 can be constructed of a material that is biocompatible and hermetically sealed, such as titanium, tantalum, stainless steel, plastic, ceramic, or the like. In some examples, pump 102 can further include one or more sensors and may be enabled for bidirectional flow of fluid through the catheter to inhibit formation of occlusions and/or for monitoring of biomarkers with the one or more sensors.

Figure 3:
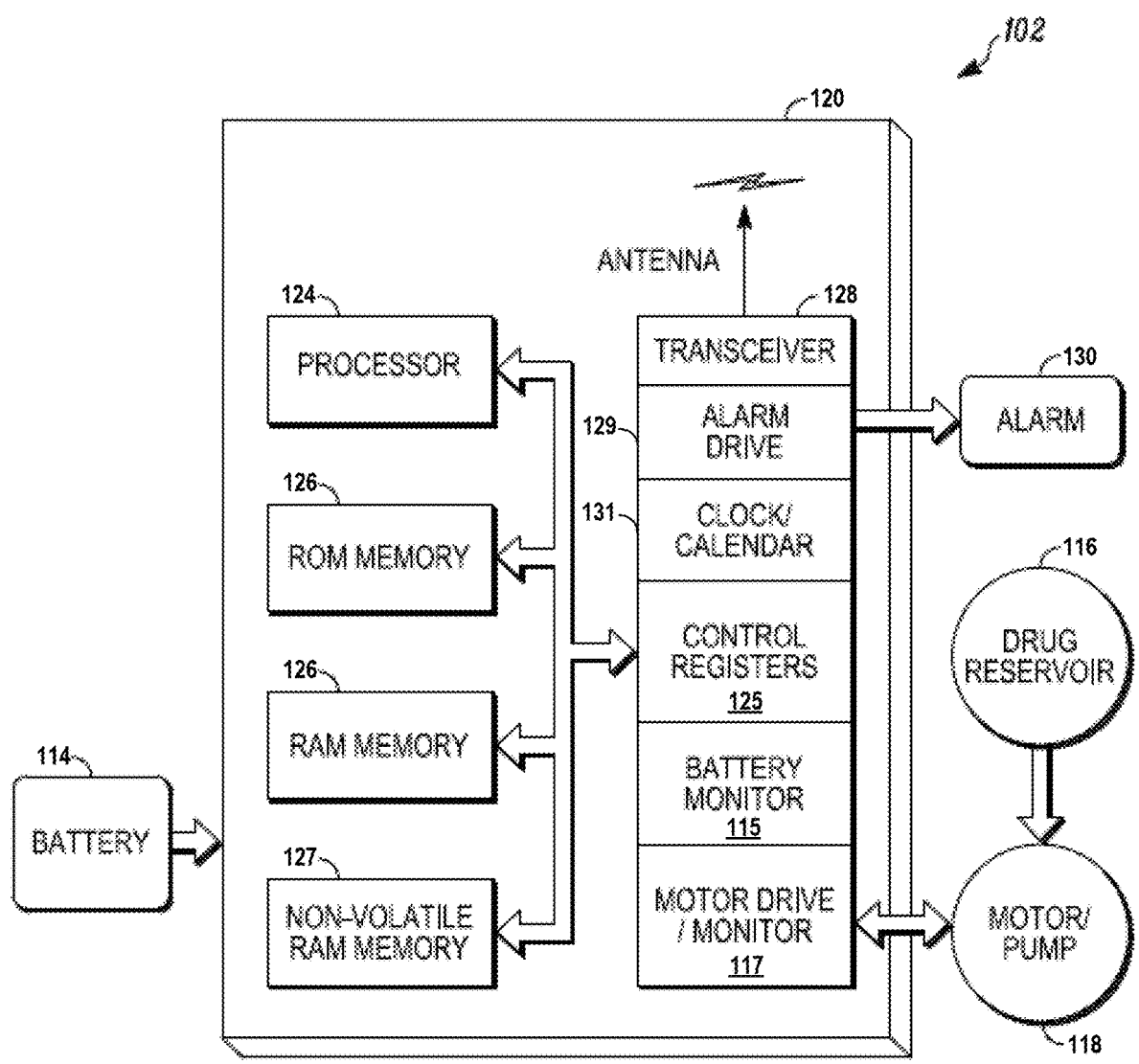
FIG. 3 is a block diagram depicting an implantable medical pump in accordance with an embodiment of the disclosure.

Referring to FIG. 3, a block diagram of an implantable medical pump 102 is depicted in accordance with an embodiment of the disclosure. The electronic components of the device 120 can be carried in the housing 112 and can be in electrical communication with the pump mechanism 118 and power source 114. The power source 114 can be a battery, such as a lithium-ion battery. The power source 114 can be carried in the housing 112 and can operate the pump mechanism 118 and electronics 120. A battery monitor 115 can monitor a battery power of the battery and a motor drive monitor 117 can monitor operation of the pump mechanism motor.

The electronic components 120 can include a processor 124, memory 126/127, and transceiver circuitry 128 that can interface with one or more control registers 125. In one embodiment, the processor 124 can be an Application-Specific Integrated Circuit (ASIC) state machine, gate array, controller, microprocessor, CPU, or the like. The electronic components 120 can be generally configured to control infusion of medicament with the pump mechanism 118 according to programmed parameters or a specified treatment protocol. The programmed parameters or specified treatment protocol can be stored in the memory 126. In some examples, electronic components 120 can further be configured to enable bidirectional flow of fluid through a catheter 104 to inhibit formation of occlusions and/or for monitoring of biomarkers. The transceiver circuitry 128 can be configured to receive information from and transmit information to the external programmer 108 and/or server 110. In embodiments, the electronic components 120 can be further be configured to operate a number of other features, such as, for example, a patient alarm 130 operable with an internal clock and/or calendar 131 and an alarm drive 129.

The implantable medical pump 102 can be configured to receive programmed parameters and other updates from the external programmer 108, which can communicate with the implantable medical pump 102 through well-known techniques such as wireless telemetry. In some embodiments, the external programmer 108 can be configured for exclusive communication with one or more implantable medical pumps 102. In other embodiments, the external programmer 108 can be any computing platform, such as a mobile phone or tablet. In some embodiments, the implantable medical pump 102 and external programmer 108 can further be in communication with a cloud-based server 110. The server 110 can be configured to receive, store and transmit information, such as program parameters, treatment protocols, drug libraries, and patient information, as well as to receive and store data recorded by the implantable medical pump 102.

Figure 4:
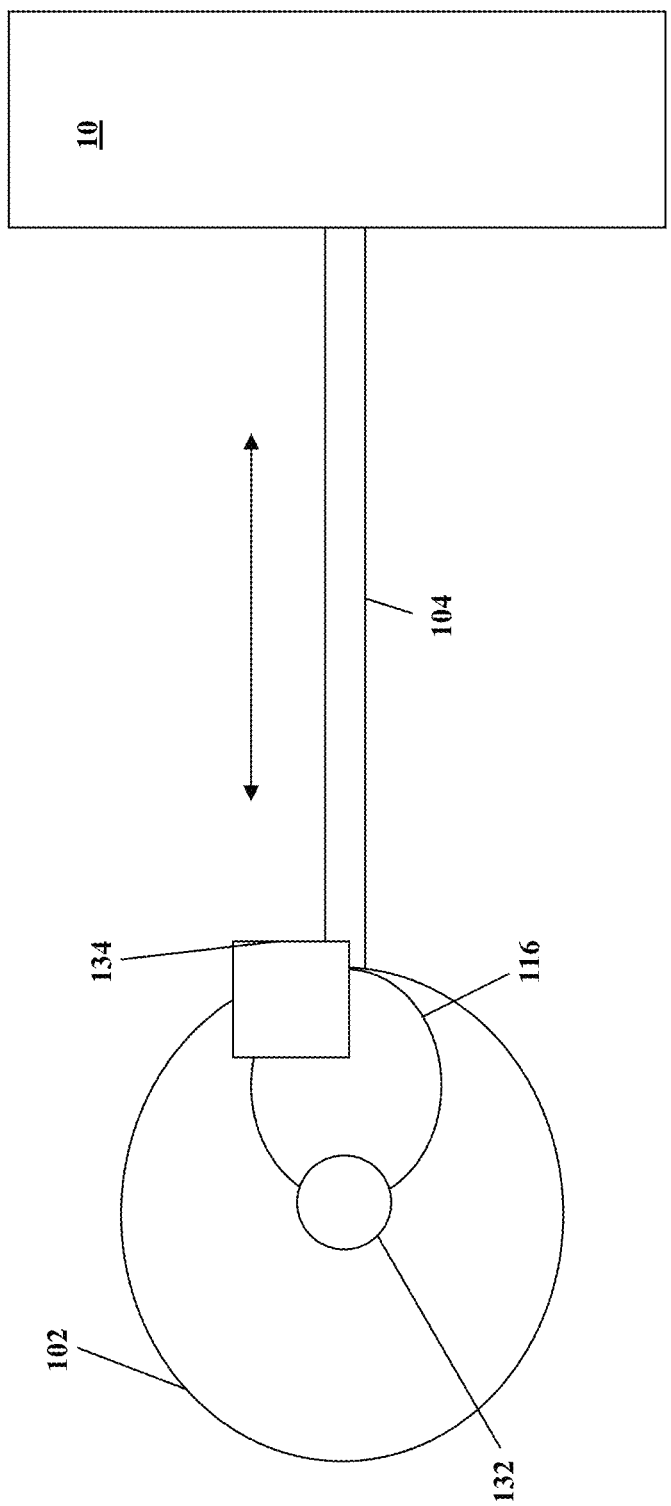
FIG. 4 is a schematic representation of an implantable medical pump in accordance with an embodiment of the disclosure.

FIG. 4 depicts a schematic representation of an implantable medical pump 102 according to an embodiment of the disclosure. Pump 102 can include a port 132 providing access to a reservoir 116 that can contain a medicament for delivery to a target location 10 in the body with a catheter 104. Pump mechanism 118 of pump 102 can also be run in reverse to aspirate fluid (e.g., CSF) into the reservoir 102 from the target location (e.g., the intrathecal space) through the catheter 104. In other embodiments, a separate pump or other mechanism can be disposed within pump 102 to aspirate fluid. In this manner, the pump 102 can provide for back and forth flow of fluid to maintain frequent or continuous fluid flow or boluses of fluid flow at regular intervals. In some embodiments, the processor can be configured to provide generally continuous fluid flow by automatically filling the reservoir with fluid from the target location and delivering the fluid back to the target location whenever the reservoir does not contain a medicament. In other embodiments, the processor can be configured to provide continual fluid flow at regular intervals with periods without fluid flow in between each interval.

Bidirectional fluid flow enables the pump 102 to maintain regular flow of fluid through the catheter 102 even after all of the medicament in the reservoir 116 has been delivered to create an "active port" that keeps fluid flow continuing without infusing a medicament or saline into the pump 102 via access port 132. This regular flow can help prevent occlusions from occurring at the catheter 104 in the target location 10 In addition, if medicament refill visits are missed by the patient, bodily fluid at the target location such as CSF can be used to keep the pump mechanism functioning rather than having the pump operate with no fluid, which could lead to pump damage requiring replacement, and rather than otherwise requiring the patient to inject saline to keep the pump mechanism functioning. In the configuration depicted in FIG. 4, catheter 104 includes a single lumen that provides for bi-directional fluid flow into and out of reservoir Still referring to FIG. 4, pump 102 can further include a sensor 134 disposed adjacent the reservoir 116 and the catheter 104 to measure biomarkers in the fluid flowing into and out of the reservoir 116. Unidirectional pumps do not have the practical ability to measure biomarkers because they function only to push medicament out of the pump and into the body, whereas a pump 102 as disclosed herein that can run in reverse to aspirate bodily fluid such as CSF into the body can measure biomarkers in the bodily fluid when the fluid is aspirated into and/or out of the pump in the presence of an appropriate sensor. Various biomarkers can be measured relative to various conditions, such that the pump can serve both to deliver a medicament to address a condition and to provide disease state monitoring technology for the treated and/or other conditions. In embodiments, exemplary biomarkers and/or conditions that can be monitored can include, for example, fluid pressure, pH, concentration of solutes, such as, for example, salt content, and the presence of proteins or other molecules. In various embodiments, data relating to the biomarkers detected by the sensor can be wirelessly transmitted to an external programming device and/or can be stored in memory for later transfer to an external device.

Figure 5:
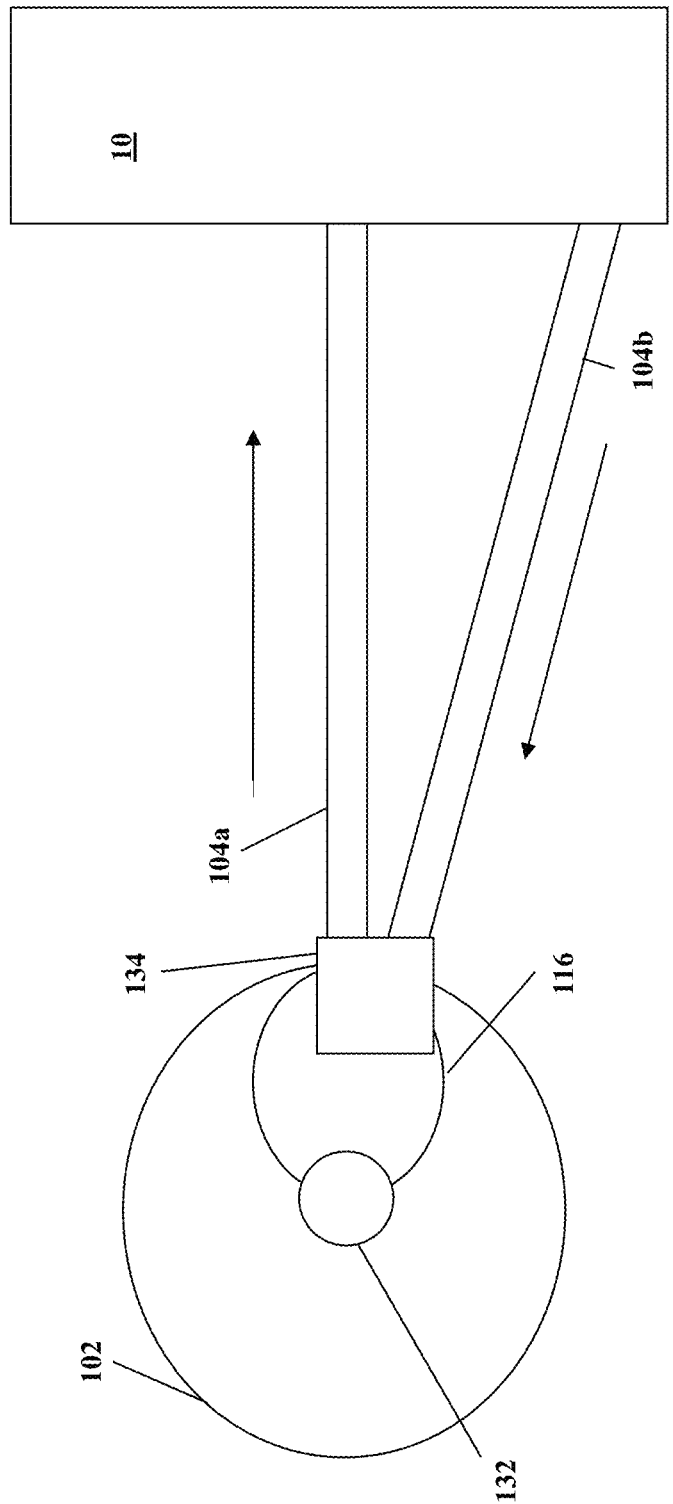
FIG. 5 is a schematic representation of an implantable medical pump in accordance with an embodiment of the disclosure.

FIG. 5 depicts another configuration of implantable medical pump 102 according to the disclosure. In this configuration, reservoir 116 of pump is in communication with a first catheter 104a extending to a first area in the target location and a second, separate catheter 104b extending to a second area in the target location. As indicated by the arrows in the figure, in this embodiment the first catheter 104a can be configured for fluid flow in a first direction (e.g., to the target location) and the second catheter 104b configured for fluid flow in the opposite direction (e.g., from the target location). In embodiments, both catheters 104a, 104b can be single lumen catheters configured for unidirectional flow. Alternatively, one or both catheters could be configured for bidirectional flow as set forth above. In this configuration, sensor 134 is positioned across the catheters 104, 104b to sense fluid flowing through both catheter 104a and catheter 104b. By accessing and enabling fluid flow to and/or from multiple areas in the target location, this configuration enables monitoring of additional biomarkers such as pressure differences to monitor for differences across areas in an anatomical feature. Similar measurements can also indicate projected useful time remaining for the catheter by correlating pressure difference or transient pressure differences with failure modes such as kinking, tissue growth, or occlusions in general. For example, if the pressure difference is increasing, an expected failure time could be anticipated. If a transient pressure is increasing, it could indicate a kink in the catheter that could be associated with an expected failure date.

Figure 6:
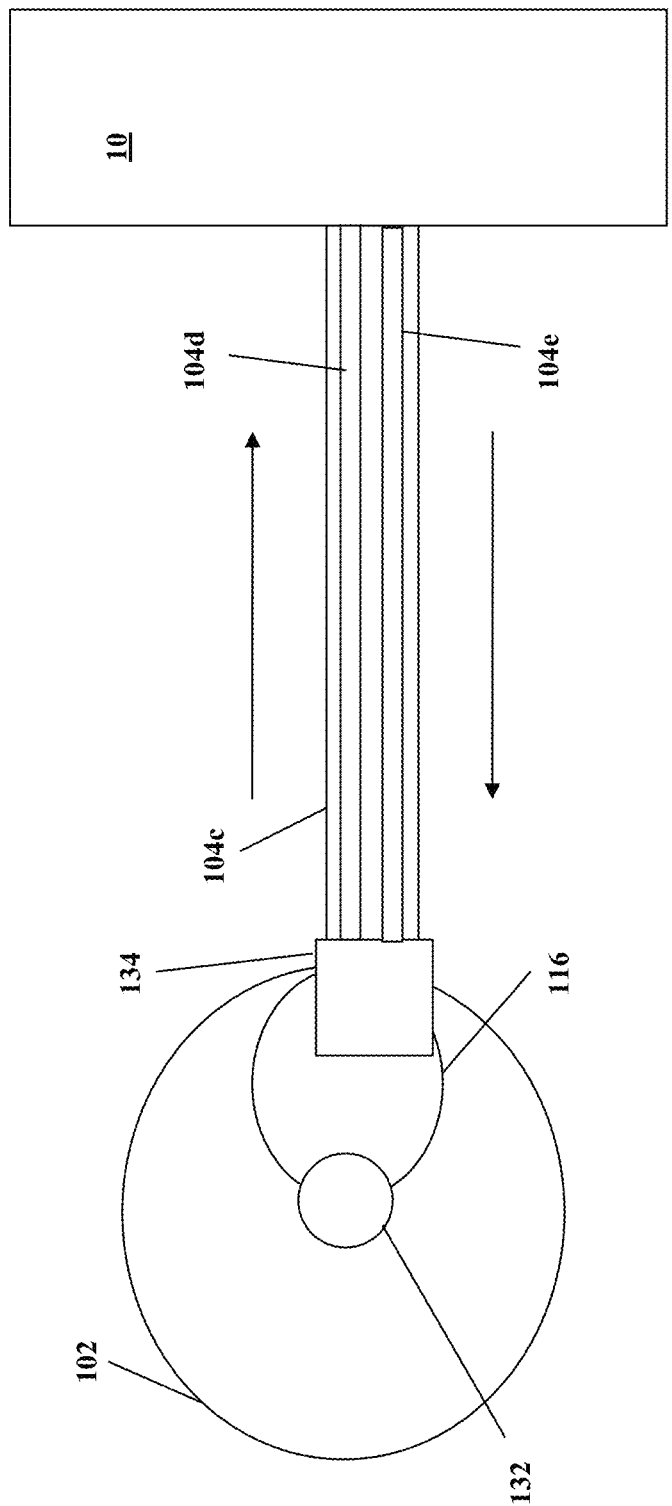
FIG. 6 is a schematic representation of an implantable medical pump in accordance with an embodiment of the disclosure.

Referring now to FIG. 6, another configuration of implantable medical pump 102 according to the disclosure is depicted. In this configuration, pump 102 includes a multi-lumen catheter 104c having a first lumen 104d for delivery of fluid to the target location 10 and a second lumen 104e for aspirating fluid from the target location 10 back to the reservoir 116. In other embodiments, one or both lumens 104d, 104e can provide bidirectional flow. Sensor 134 can be positioned to be in communication with both lumens 104d, 104e in order to monitor additional parameters such as pressure differences as discussed above.

Pumps 102 as disclosed herein accomplish bidirectional fluid flow that can deliver a medicament from a reservoir and aspirate bodily fluid such as CSF into and out of the same reservoir such that no separate pump reservoir is needed in order to provide continuous or continual fluid flow. Rather, the existing medicament reservoir can be used to temporarily store the bodily fluid when it is not storing a medicament. Such a system provides numerous benefits, including providing regular or continuous fluid flow without frequent injections to fill the reservoir to address concerns regarding tissue encapsulation/occlusions, providing an opportunity to measure biomarkers continuously or intermittently, and providing an opportunity to reverse fluid flow direction to clear occlusions at the distal end of the catheter (i.e., push out tissue that grows in).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

The invention claimed is:

1. An implantable medical pump comprising:
   a pump housing configured to be subcutaneously implanted into a body of a patient;
   a medicament reservoir contained within the pump housing, wherein the medicament reservoir is configured to contain a medicament;
   at least one catheter extending from the pump housing to a target location in the body of the patient, wherein the at least one catheter is in fluid communication with the medicament reservoir;
   a pump mechanism; and
   a processor configured to control the pump mechanism to:
      deliver the medicament from the medicament reservoir to the target location;
      aspirate a fluid from the target location back into the medicament reservoir; and
      deliver the fluid from the medicament reservoir back to the target location.

2. The implantable medical pump of claim 1, wherein the processor is configured to provide a generally continuous fluid flow through the at least one catheter by causing the pump mechanism to aspirate the fluid from the target location into the medicament reservoir and deliver the fluid from the medicament reservoir back to the target location when the medicament reservoir does not contain the medicament.

3. The implantable medical pump of claim 1, wherein the processor is configured to provide a generally continuous fluid flow through the at least one catheter by causing the pump mechanism to periodically aspirate the fluid from the target location into the medicament reservoir and periodically deliver the fluid from the medicament reservoir back to the target location at regular intervals when the medicament reservoir does not contain the medicament.

4. The implantable medical pump of claim 1, wherein the at least one catheter comprises a single catheter having a single lumen configured to both:
   deliver the medicament and the fluid from the medicament reservoir to the target location; and
   aspirate the fluid from the target location into the medicament reservoir.

5. The implantable medical pump of claim 1, wherein the at least one catheter comprises:
   a first catheter configured to deliver the medicament and the fluid from the medicament reservoir to the target location; and
   a second catheter configured to aspirate the fluid from the target location into the medicament reservoir.

6. The implantable medical pump of claim 1, wherein the at least one catheter comprises a single multi-lumen catheter having:
   a first lumen configured to deliver the medicament and the fluid from the medicament reservoir to the target location; and
   a second lumen configured to aspirate the fluid from the target location into the medicament reservoir.

7. The implantable medical pump of claim 1, further comprising a refill port disposed on an exterior surface of the pump housing, wherein the refill port is configured to provide percutaneous access to refill the medicament reservoir with the medicament.

8. An implantable medical pump comprising:
   a pump housing configured to be subcutaneously implanted into a body of a patient;
   a medicament reservoir contained within the pump housing, wherein the medicament reservoir is configured to contain a medicament;
   at least one catheter extending from the pump housing to a target location in the body of the patient, wherein the at least one catheter is in fluid communication with the medicament reservoir;
   a pump mechanism;
   a processor configured to control the pump mechanism to:
      deliver the medicament from the medicament reservoir to the target location;
      aspirate a fluid from the target location back into the medicament reservoir; and
      deliver the fluid from the medicament reservoir back to the target location; and
   a sensor configured to sense one or more biomarkers in the fluid.

9. The implantable medical pump of claim 8, wherein the processor is further configured to wirelessly transmit data relating to the one or more biomarkers to an external device.

10. The implantable medical pump of claim 8, wherein the processor is further configured to store data relating to the one or more biomarkers in a memory disposed within the pump housing.

11. The implantable medical pump of claim 8, wherein the at least one catheter comprises a single catheter having a single lumen configured to deliver the medicament to the target location and to aspirate the fluid from the target location into the medicament reservoir.

12. The implantable medical pump of claim 8, wherein the at least one catheter comprises:
   a first catheter configured to deliver the medicament and the fluid to the target location; and
   a second catheter configured to aspirate the fluid from the target location into the medicament reservoir.

13. The implantable medical pump of claim 8, wherein the at least one catheter comprises a single multi-lumen catheter having:
   a first lumen configured to deliver the medicament and the fluid from the medicament reservoir to the target location; and
   a second lumen configured to aspirate the fluid from the target location into the medicament reservoir.

14. The implantable medical pump of claim 8, further comprising a refill port disposed on an exterior surface of the pump housing, wherein the refill port is configured to provide percutaneous access to refill the medicament reservoir with the medicament.

15. The implantable medical pump of claim 8, wherein the processor is configured to cause the pump mechanism to aspirate the fluid from the target location into the medicament reservoir when the medicament reservoir does not contain the medicament.

16. The implantable medical pump of claim 15, wherein the processor is configured to provide a generally continuous fluid flow through the at least one catheter by causing the pump mechanism to aspirate the fluid from the target location into the medicament reservoir when the medicament reservoir does not contain the medicament.

17. The implantable medical pump of claim 15, wherein the processor is configured to provide a generally continual fluid flow through the at least one catheter by causing the pump mechanism to periodically aspirate the fluid from the target location into the medicament reservoir at regular intervals when the medicament reservoir does not contain the medicament.

* * * * *